(12) United States Patent
Borsotti et al.

(10) Patent No.: US 9,650,327 B2
(45) Date of Patent: May 16, 2017

(54) PROCESS FOR THE SELECTIVE HYDROGENATION OF VEGETABLE OILS

(71) Applicant: Novamont S.p.A., Novara (IT)

(72) Inventors: Giampietro Borsotti, Novara (IT); Luigi Capuzzi, Novara (IT); Francesca Digioia, Barengo (IT)

(73) Assignee: NOVAMONT S.P.A., Novara (IT)

( * ) Notice: Subject to any disclaimer, the term of this patent is extended or adjusted under 35 U.S.C. 154(b) by 0 days.

(21) Appl. No.: 14/900,762

(22) PCT Filed: Jun. 25, 2014

(86) PCT No.: PCT/EP2014/063384
§ 371 (c)(1),
(2) Date: Dec. 22, 2015

(87) PCT Pub. No.: WO2014/207038
PCT Pub. Date: Dec. 31, 2014

(65) Prior Publication Data
US 2016/0137580 A1    May 19, 2016

(30) Foreign Application Priority Data

Jun. 27, 2013   (IT) .............................. NO2013A0005

(51) Int. Cl.
*C07C 51/36* (2006.01)
*C11C 3/12* (2006.01)
*B01J 23/44* (2006.01)

(52) U.S. Cl.
CPC ............... *C07C 51/36* (2013.01); *B01J 23/44* (2013.01); *C11C 3/126* (2013.01)

(58) Field of Classification Search
None
See application file for complete search history.

(56) References Cited

U.S. PATENT DOCUMENTS 4,179,454 A * 12/1979 Mehta ................. C11C 1/025
554/144
7,498,453 B2 * 3/2009 Van Toor ............... A23D 7/001
554/141

FOREIGN PATENT DOCUMENTS

WO    WO-2011/080296 A1    7/2011

OTHER PUBLICATIONS

Santacesaria et al., Role of mass transfer and kinetics in the hydrogenation fo rapeseed oil on a supported palladium catalyst, 1994, Applied Catalysis S: General, No. 116, pp. 269-294.*
Nohair et al., Palladium supported catalyst for the selective hydrogenation of sunflower oil, 2005, Journal of Molecular Catalysis, A: Chemical, No. 229, pp. 117-126.*
Hsu, et al., Heterogeneous catalytric hydrogenation of canola oil using palladium, 1986, JAOCS, vol. 63, No. 8, pp. 1036-1042.*
Macher, et al., Hydrogenationof palm oin in near-critical and supercritical propane, 2001, Eur. J. Lipid. Sci. Technol., vol. 103, pp. 81-84.*
Kirk-Othmer, 1993, Encyclopedia of chemcial Technology, fourth edition, vol. 10 pp. 267.*
Duan et al., "Catalytic hydrotreatment of crude algal bio-oil in supercritical water", Applied Catalysis B: Environmental, vol. 104, No. 1, Feb. 16, 2011), pp. 136-143.
Duan et al., "Upgrading of crude algal bio-oil in supercritical water", Bioresourse Technology, vol. 102, No. 2, Jan. 1, 2011, pp. 1899-1906.

* cited by examiner

Primary Examiner — Yate K Cutliff
(74) Attorney, Agent, or Firm — Polsinelli PC

(57) ABSTRACT

This invention relates to a process for the selective hydrogenation of vegetable oils. In particular the invention relates to a process for the hydrogenation of vegetable oils which is capable of selectively converting polyunsaturated fatty acids into mono-unsaturated fatty acids and products obtained therefrom. The vegetable oils obtained from the process according to the invention have in particular a high mono-unsaturated fatty acids content and are particularly suitable for use as raw materials for the synthesis of chemical intermediates.

19 Claims, No Drawings

PROCESS FOR THE SELECTIVE HYDROGENATION OF VEGETABLE OILS

CROSS REFERENCE TO RELATED APPLICATIONS

This application is a National Phase filing under 35 U.S.C. §371 of PCT/EP2014/063384 filed on Jun. 25, 2014; and this application claims priority to Application No. NO2013A000005 filed on Jun. 27, 2013 in Italy. The entire contents of each application are hereby incorporated by reference.

This invention relates to a process for the selective hydrogenation of vegetable oils. In particular this invention relates to a process for the hydrogenation of vegetable oils which is capable of selectively converting polyunsaturated fatty acids into mono-unsaturated fatty acids and the products obtained therefrom. The vegetable oils obtained by the process according to the invention have in particular a high mono-unsaturated fatty acids content and are particularly suitable for use as raw materials for the synthesis of chemical intermediates. Vegetable oils are now an important raw material for the chemical industry on account of the increasingly pressing need to identify raw materials of renewable origin which are alternatives to conventional oil-based sources.

For example WO2008/138892 describes a process of oxidative cleavage which, starting from vegetable oils containing mono-unsaturated fatty acid triglycerides, makes it possible to produce intermediates which are important for the preparation of polyesters, such as for example the saturated dicarboxylic acids azelaic acid or brassylic acid.

As is known, vegetable oils comprise mixtures of fatty acid triglycerides. These fatty acids generally contain from 16 to 22 carbon atoms and may be saturated, for example stearic acid, mono-unsaturated, for example oleic acid, or polyunsaturated, such as for example linoleic acid and linolenic acid.

These vegetable oils have quite different compositions, depending upon the nature of the plant species from which they are obtained, for example different types and contents of mono-unsaturated fatty acids. This constitutes an appreciable limitation on the use of vegetable oils as raw materials for the organic chemical industry.

It has therefore become necessary to find and make use of processes to modify the composition of vegetable oils in order to encourage their use in this sector.

For example, hydrogenation processes have wide application in the chemical field, and in particular in the field of oil chemistry. The double bonds present in the chains of unsaturated fatty acids can in fact be saturated by the addition of hydrogen in the presence of catalysts such as for example nickel, platinum, palladium or copper. The hydrogenation processes are exothermic and the reaction rate depends on the type of oil, the temperature, the activity and concentration of the catalyst, and the hydrogen pressure. Although widely used, these processes nevertheless have appreciable limitations from the point of view of selectivity. In particular the possibility of maintaining high conversions of polyunsaturated fatty acids while avoiding the formation of saturated fatty acids is limited.

There is therefore a need to develop new selective hydrogenation processes for vegetable oils which are capable of selectively converting polyunsaturated fatty acids into mono-unsaturated fatty acids.

Starting from this problem it has now surprisingly been discovered that in the presence of a catalyst based on palladium metal, the addition of specific quantities of water makes it possible to modify the progress of the hydrogenation reaction in such a way as to significantly increase the conversion of the polyunsaturated fatty acids of the triglycerides present in the oil while at the same time increasing or at least maintaining the selectivity for mono-unsaturated fatty acids.

In particular this invention relates to a process for the catalytic hydrogenation of vegetable oils in which the oil is placed in contact with molecular hydrogen in the presence of a catalyst comprising supported palladium metal, characterised in that the process is performed in the presence of an amount of water comprised between 5:1 and 100:1 with respect to the weight of the palladium metal.

It has in fact been surprisingly discovered that the presence of specific quantities of water is capable of improving the catalytic activity and selectivity of catalysts comprising palladium metal in relation to the hydrogenation of polyunsaturated fatty acids from the triglycerides present in an oil.

Without wishing to be bound to any specific theory, it is believed that the presence of water during the hydrogenation process may encourage saponification reactions for the triglycerides in the vegetable oil, the products of which promote the selectivity of the hydrogenation reaction. This makes it possible to use the process according to this invention to selectively convert polyunsaturated fatty acids into mono-unsaturated fatty acids, thus reducing the formation of saturated fatty acids.

This effect can among other things be revealed by comparing the state of progress of the reaction at a predetermined reaction time, for example 80 minutes, according to whether the reaction is performed with or without the presence of specific quantities of water.

Thanks to the process according to this invention it is therefore possible to obtain an oil having a high mono-unsaturated fatty acids content that is particularly suitable for subsequent use as a raw material for the synthesis of chemical intermediates.

The vegetable oil obtained from the process of the present invention is particularly useful as starting material, even in mixture with other vegetable oils, for oxidative cleavage processes using inorganic and organic peroxides, peracids, nitric acid, permanganates, periodates, $O_2$, $O_3$ or gaseous mixtures containing thereof as oxidizing agents. Oxidative cleavage processes using peroxides, such as hydrogen peroxides, and $O_2$ or mixtures containing $O_2$ as oxidizing agents are preferred. Specific examples are the oxidative cleavage processes described in applications WO 2008/138892, WO 2011/080296 or WO 2013/079849 A1.

The vegetable oil obtained from the process of the present invention is more particularly useful as starting material for oxidative cleavage process comprising the steps of:
 a) causing the unsaturated carboxylic acid triglycerides to react with an oxidising compound, preferably in the presence of a catalyst capable of catalysing the reaction of oxidising the olefin double bond to obtain an intermediate compound containing vicinal diols;
 b) causing the said intermediate compound to react with oxygen, or a gaseous mixture containing oxygen, preferably in the presence of a catalyst capable of catalysing the reaction of oxidising the vicinal diols to carboxyl groups obtaining saturated monocarboxylic acids and triglycerides containing saturated dicarboxylic acids.

When the vegetable oil obtained from the process of the present invention is used in mixtures with other vegetable oils as starting material for oxidative cleavage processes, preferably said mixtures contain more than 10% of the vegetable oil obtained from the process of the present invention.

The water can be introduced before the beginning of the reaction or progressively over the course of the reaction. For example, the presence of suitable quantities of water can be obtained by feeding specified amounts of hydrogen gas previously saturated with water into the hydrogenation reactor. In the process according to the present invention the quantity of water is comprised, or varies between 5:1 and 100:1, preferably 7:1 and 50:1, more preferably 10:1 and 40:1, advantageously 15:1 and 37:1, with respect to the weight of the palladium metal.

By using the process according to this invention it is possible to hydrogenate vegetable oils such as: soya oil, olive oil, castor oil, sunflower oil, peanut oil, maize oil, palm oil, jatropha oil, cardoon oil such as from *Cynara cardunculus, Sylibum marianum*, cuphea oil, Brassicaceae oils such as from *Crambe abyssinica, Brassica carinata, Brassica napus* (rape), *Lesquerella*, or mixtures thereof. Waste frying oils or other exhausted vegetable oils can also be hydrogenated according to this invention. The use of sunflower oil, Brassicaceae oils, or cardoon oils such as those from *Cynara cardunculus* and *Sylibum marianum* is particularly preferred.

In particular the latter are obtained from plant species belonging to the Cardoon family, which are very robust annual or perennial herbaceous plants having the further advantage that they can be cultivated in arid areas with poorly favourable climates.

The catalysts for the process according to this invention comprises supported palladium metal and may be used in the form of sheets, particles or spheres having dimensions typically between 2 and 4 mm. The quantity of palladium metal is preferably between 30 mg/kg and 500 mg/kg, more preferably between 40 and 70 mg/kg, with respect to the quantity of vegetable oil which has to be hydrogenated and may vary within that range depending upon the nature of the catalyst, its surface area and the concentration of palladium metal with respect to any support.

Typically the catalyst comprises 0.1-1% by weight of palladium metal; preferably the catalyst comprises 0.1-0.5% by weight of palladium metal.

Preferably the catalyst comprises palladium metal in a form supported for example on alumina, carbon in various forms including nanotubes, $CeO_2$, $ZrO_2$, $CrO_2$, $TiO_2$, silica, inorganic-organic sol-gel matrices, polycrystalline oxide substrates, amorphous carbon, zeolites, aluminosilicates, alkaline earth carbonates such as magnesium carbonate, calcium carbonate or barium carbonate, barium sulphate, montmorillonites, polymer matrices, multifunctional resins, and ceramic supports. In a preferred form of the process the catalyst comprises palladium metal supported on alumina or on carbon.

The catalyst may be prepared according to any techniques known to those skilled in the art, for example by finely dispersing a palladium salt on the support and subsequently reducing the palladium salt to palladium metal. The stage of dispersing the palladium salt may for example be performed by impregnation, adsorption from a solution, co-precipitation or deposition, for example by chemical vapour deposition. The stage of reducing the palladium salt is typically performed by heating the supported palladium salt in the presence of an atmosphere of molecular hydrogen. The stage of catalyst preparation may be performed separately from the hydrogenation process according to this invention or may take place in a preliminary stage thereof. For example the supported palladium salt may be placed in the hydrogenation reactor and reduced in situ in a hydrogen atmosphere before adding the vegetable oil. Suitable catalysts for use in the process according to this invention are for example palladium supported on γ-alumina containing 0.2% by weight of palladium ("G68G" produced by Sud Chemie) and palladium supported on γ-alumina containing 0.5% by weight of palladium in 2.4-4 mm spheres ("AMS-5" produced by Engelhard).

The advantages of the process according to this invention include the fact that it can be performed without the need to add promoters such as for example copper, silver, zinc, tin, titanium, zirconium, hafnium, vanadium, niobium, tantalum, chromium, molybdenum, tungsten or manganese to the catalyst in order to improve selectivity.

In general the process according to this invention may be performed in one or more suitable items or apparatus such as for example stirred reactors, fixed bed reactors, mobile bed reactors, entrained flow reactors and fluidised bed reactors. At the end of the reaction the catalyst can be readily recovered by means of known techniques and reused several times. In a preferred embodiment the process for the catalytic hydrogenation of vegetable oils of the present invention comprises a step wherein the catalyst is separated from the vegetable oil, for example by filtration or settling.

In the case of stirred reactors in particular, stirring of the medium helps to determine the rate of diffusion of hydrogen and the amount of contact between the vegetable oil and the hydrogen. Depending upon the volume and configuration of the reactor, stirring speeds of for example from 100 to 1200 rpm, more particularly from 200 to 1000 rpm, may be used.

The hydrogenation reaction according to the present invention is preferably performed at temperatures from 0 to 130° C.

The temperature may be controlled for example by heating the reaction mixture before the start of the reaction. Because the hydrogenation reaction is exothermic the progress of the reaction gives rise to a gradual increase in temperature within the reaction mixture. This increase is typically controlled through cooling systems which prevent it from becoming excessively heated, which could have an adverse effect on the course of the reaction.

As far as molecular hydrogen is concerned, the hydrogenation reaction is preferably performed at molecular hydrogen pressures of from 1 to 15 bar. Depending on requirements, the hydrogen can be inserted into the reactor continuously, regulating the flow, or fed in one or more aliquots, for example 3, 5 or 7 aliquots, preferably in 1 to 10 aliquots, while nevertheless maintaining the hydrogen pressure within the range indicated above.

The process can be performed in the presence of organic solvents. Suitable organic solvents are selected from hydrocarbons, esters, ketones. Preferred organic solvents are easily recoverable, for example by distillation.

Additives such as bases can be added in order to further improve the selectivity of the hydrogenation reaction as known in the art. Examples of said bases are amines, oxides, hydroxydes, or carbonates of alkali metals, alkaline earth metals or ammonium. Specific examples of bases are N-ethyldiisopropylamine, triethylamine, diamines such as ethylenediamine, its homologues and/or derivatives such as tetramethylethylenediamine, tetraalkyl amines, where the alkyl chain are for example C2 to C6 alkyl chains, cyclic amines such as diazabicyclooctane or diazabicycloundecene, ammonium hydroxide salts such as choline or tetrabutylammonium hydroxide. Choline or tetrabutylammonium hydroxide are advantageously used in the presence of a co-solvent such as methanol when petroleum ether is used as solvent for the vegetable oil. In this case the methanol solubilizes the tetrabutylammonium hydroxide and forms a separated phase in which the catalyst will partition at the end of the reaction, facilitating the recovery.

The process can be controlled in a manner known to those skilled in the art, for example by measuring the pressure within the reactor and interrupting the reaction when a specific quantity of hydrogen has been absorbed.

As an alternative the course of the reaction can be monitored by sampling and analysing the composition of the reaction mixture. The theoretical amount of hydrogen required for the completion of the reaction can be easily determined on the basis of the composition of the starting vegetable oil for example by analyzing the amount of unsaturations.

The duration of the process according to this invention depends on the nature of the vegetable oil, the operating conditions, the desired conversion, and the dimensions of the reactor used, and is typically from 5 minutes to 6 hours, for example from 60 to 300 minutes.

In the course of the reaction it is possible that reactions isomerising the unsaturated fatty acids present in the vegetable oil may take place. As is known, the unsaturated fatty acids present in vegetable oils in nature are mainly of the cis type. Under high temperature conditions these cis acids can engage in isomerisation reactions and become converted into trans isomers. In general the trans isomers have higher melting points than the cis isomers and beyond particular levels of conversion this can give rise to the formation of a solid phase which for example contains trans 9-octadecenoic acid.

When compared to naturally occurring vegetable oils, the vegetable oil containing trans isomers are also less susceptible to oxidation reactions by peroxides. This determines longer reaction times when said oils are subjected to oxidative cleavage reactions.

According to a preferred embodiment of the present invention, the hydrogenation reaction is preferably performed at temperatures from 70 to 130° C., more preferably from 100 to 130° C., and preferably maintaining molecular hydrogen pressures from 1 to 6 bar, more preferably from 3.5 to 6 bar. According to this embodiment, the hydrogen can be inserted into the reactor continuously, regulating the flow, or fed in one or more aliquots, preferably in 1 to 10 aliquots, while nevertheless maintaining the hydrogen pressure within the range indicated above. Stirring speeds preferably from 200 to 500 rpm are used.

According to another preferred embodiment of the present invention, the hydrogenation reaction is preferably performed at temperatures from 0 to 50° C., more preferably from 0 to 30° C., even more preferably from 0 to 20° C., preferably maintaining molecular hydrogen pressures of between 1-2 bar, more preferably of between 1-1.5 bar and in the presence of an organic solvent to decrease the viscosity of the system. Suitable organic solvents are selected from hydrocarbons, esters, ketones. Preferred organic solvents are easily recoverable, for example by distillation. Specific examples of suitable organic solvents are petroleum ether, hexane, ethyl acetate, toluene, etc. The organic solvent:oil weight ratio is preferably from 0.5:1 to 3:1, more preferably from 1:1 to 2:1.

According to this embodiment, stirring speeds of from 500 to 1000 rpm are preferably used. When the hydrogenation reaction is performed at low temperatures according to the current embodiment, particularly high conversion of polyunsaturated acids and high selectivity towards mono-unsaturated acids are achieved, even without the need of additives such as amines.

When a vegetable oil is hydrogenated according to this embodiment, the resulting hydrogenated oil has a di-unsaturated and mono-unsaturated acid content and a cis isomer content which render it particularly suitable to be subjected to oxidative cleavage processes, preferably those using peroxides, such as hydrogen peroxides, and $O_2$ or mixtures containing $O_2$ as oxidizing agents. Specifically, said oils are particularly suitable to be used as starting material for the oxidative cleavage processes described in WO 2008/138892, WO 2011/080296 or WO 2013/079849). Preferably said oil is characterized by:
  a di-unsaturated acid content of less than 10% by weight, preferably less than 5%, with respect to the total fatty acids content;
  a mono-unsaturated acid content of more than 70% by weight with respect to the total fatty acids content, preferably of more than 75%, of which 9-cis and 12-cis isomers are preferably more than 80%, more preferably more than 85%;
  a trans mono-unsaturated isomer content higher than 1.5% and lower than 12%, preferably higher than 2% and lower than 10% by weight with respect to the total fatty acids content.

The present invention also refers to a vegetable oil characterized by:
  a di-unsaturated acids content of less than 10% by weight, preferably less than 5%, with respect to the total fatty acids content;
  a mono-unsaturated acid content of more than 70% by weight with respect to the total fatty acids content, preferably of more than 75%, of which, of which 9-cis and 12-cis isomers are preferably more than 80%, more preferably more than 85%;
  a trans mono-unsaturated isomer content higher than 1.5% and lower than 12%, preferably higher than 2% and lower than 10% by weight with respect to the total fatty acids content,
which is particularly suitable to be used as starting material for oxidative cleavage processes to produce intermediates useful for the preparation of polyesters. Particularly, a trans monounsaturated acid content of the oil of from 1.5% to 12% allows to perform oxidative cleavage processes using hydrogen peroxide and/or $O_2$ as oxidizing agents without affecting the reaction times.

Said oil can be advantageously obtained by subjecting a vegetable oil, preferably a cardoon oil, to the hydrogenation reaction of the invention at temperatures of from 0 to 50° C., preferably from 0 to 20° C., and in the presence of an organic solvent.

Said oil is preferably used as starting material for oxidative cleavage processes comprising the steps of:
  a) causing the unsaturated carboxylic acid triglycerides to react with an oxidising compound, preferably in the presence of a catalyst capable of catalysing the reaction of oxidising the olefin double bond to obtain an intermediate compound containing vicinal diols;
  b) causing the said intermediate compound to react with oxygen, or a gaseous mixture containing oxygen, preferably in the presence of a catalyst capable of catalysing the reaction of oxidising the vicinal diols to carboxyl groups obtaining saturated monocarboxylic acids and triglycerides containing saturated dicarboxylic acids.

The invention will now be illustrated with a number of examples which are intended to be merely illustrative and do not limit the invention.

EXAMPLES

The oil fatty acid composition in the following examples was determined after transesterification of 140 µl of oil samples in 140 µl of methanolic KOH (2N). Fatty acid methyl esters were extracted from the methanolic solutions into 3 ml hexane and then analyzed in a gas chromatograph equipped with a flame ionization detector (FID) and a SLB-IL111 100 m×0.25 mm×0.2 µm capillary column (SUPELCO) at a constant pressure of 275 kPa. Oven temperature program: 100° C. (35 min)—2.5° C./min-140° C. (30 min)—5.0°/min-260° C. (25 min) for a total run time of 130 min. Injector temperature: 250° C.; split ratio: 250:1; carrier gas: Helium.

The conversion of di-unsaturated acids (C18:2) was determined as follows:

$$\frac{\left(\sum \text{starting } C18:2 - \sum \text{final } C18:2\right)}{\sum \text{starting } C18:2},$$

wherein $\Sigma$ starting C18:2 and $\Sigma$ final C18:2 corresponded to the sum of the weight % of the various isomers of C18 diunsaturated acids with respect to the total fatty acid composition respectively before and after the hydrogenation reaction.

The selectivity towards monounsaturated acids (C18:1) was determined as follows:

$$\frac{\left(\sum \text{final } C18:1 - \sum \text{starting } C18:1\right)}{\left(\sum \text{starting } C18:2 - \sum \text{final } C18:2\right)}$$

wherein $\Sigma$ final C18:1 and $\Sigma$ starting C18:1 corresponded to the sum of the weight % of the various isomers of C18 monounsaturated acids with respect to the total fatty acid composition respectively after and before the hydrogenation reaction, and $\Sigma$ starting C18:2 and $\Sigma$ final C18:2 corresponded to the sum of the weight % of the various isomers of C18 diunsaturated acids with respect to the total fatty acid composition respectively before and after the hydrogenation reaction.

Example 1 (Comparative)

500 g of sunflower oil containing 56% by weight of linoleic acid with respect to the total fatty acids content were hydrogenated in an autoclave fitted with a stirrer in the presence of 15.5 g of catalyst based on palladium supported on γ-alumina (0.2% by weight of Pd-"G68G" produced by Sud Chemie) at a temperature of 118° C., maintaining a hydrogen pressure between 2 and 5 bar. The reaction was interrupted after 80 minutes. The conversion of linoleic acid, determined by gas chromatographic analysis, was 34.5%, with selectivity for mono-unsaturated acids of 28.9%.

Example 2

The hydrogenation reaction was performed under the same conditions as in Example 1 (comparative) with the addition of 0.37 g of water to the reaction mixture. After 80 minutes the conversion of linoleic acid was 63.4% and the selectivity for mono-unsaturated acids was 33.3%.

Example 3

The hydrogenation reaction was performed under the same conditions as in Example 1 (comparative) with the addition of 0.74 g of water to the reaction mixture. After 80 minutes the conversion of linoleic acid was 68.3% and the selectivity for mono-unsaturated acids was 35.6%.

Example 4

The hydrogenation reaction was performed under the same conditions as in Example 1 (comparative) with the addition of 1.23 g of water to the reaction mixture. After 80 minutes the conversion of linoleic acid was 37.8% and the selectivity for mono-unsaturated acids was 33.1%.

Example 5

The hydrogenation reaction was performed in a 500 ml glass flask, equipped with an electromagnetic stirrer and connected through a tube to a graduated funnel with a water head for the dosage of $H_2$.

The flask was filled with 50 g of cardoon oil, 150 ml of petroleum ether and 0.85 g of 0.3% $Pd/Al_2O_3$ catalyst in powder form (Johnson Matthey; water content 4.2% by weight).

The flask was connected to a pump to remove the air and then filled with 2.7 l of molecular hydrogen, which was bubbled through the water head in the graduated funnel and was saturated with water (at a temperature of 20-25° C.). The quantity of water fed together with the hydrogen was of 52 mg. The resulting water:metallic Pd weight ratio was of about 35:1.

The flask was vigorously stirred for 140 minutes at 700 rpm while maintaining a temperature of 5-6° C. through a cooling water bath. The catalyst was filtered off and the organic solvent was evaporated to obtain hydrogenated cardoon oil.

The weight percentage composition of the C18 fatty acids of the hydrogenated oil with respect to the total fatty acid composition as measured by GC analysis after 100 minutes and after 140 minutes of reaction, compared to the composition of the starting cardoon oil is reported in table 1.

The conversion of linoleic acid was of 85% after 100 minutes, and continued to rise up to the notable value of 94% after 140 minutes of reaction. At the end of the reaction the selectivity towards C18 monounsaturated acid was of 93.1%, the C18 monounsaturated trans isomers content was below 10%, and the sum of 9-cis and 12-cis isomers corresponded to 86.3% of the monounsaturated acids.

Example 6

The hydrogenation reaction was performed under the same conditions as in Example 5 but in the presence of 75 ml petroleum ether instead of 150 ml.

After 140 minutes the conversion of linoleic acid was 92.6%, the selectivity towards C18 monounsaturated acid was of 92.4%, and the sum of 9-cis and 12-cis isomers corresponded to 85.1% of the monounsaturated acids. The composition of the hydrogenated oil as measured by GC analysis is reported in table 1.

TABLE 1

| Fatty acid composition | Cardoon oil | Example 5 | | Example 6 |
|---|---|---|---|---|
| Hydrogenation time | — | 100 min | 140 min | 140 min |
| C 18:0 | 3.2 | 6.6 | 7.5 | 7.7 |
| C 18:1 cis | 25.6 | 65.6 | 67.8 | 65.5 |
| C 18:1 trans | — | 7.5 | 9.8 | 9.9 |
| C 18:2 | 59.4 | 8.9 | 3.6 | 4.4 |
| C 18:3 | 0.2 | — | — | — |
| Conversion C18:2 | — | 85.0% | 94.0% | 92.6% |
| Selectivity C18:1 | — | 94.1% | 93.1% | 92.4% |
| 9-cis C18:1/Σ C18:1 | 96.7% | 62.5% | 60.6% | 60.8% |
| 12-cis C18:1/Σ C18:1 | — | 26.3% | 25.7% | 24.3% |

Example 7

The hydrogenation reaction was performed in the same apparatus of Examples 5-6.

The flask was filled with 50 g of sunflower oil, 150 ml of petroleum ether and 0.85 g of 0.3% Pd/Al$_2$O$_3$ catalyst in powder form (Johnson Matthey; water content 4.2% by weight).

The flask was connected to a pump to remove the air and then filled with 2.5 l of molecular hydrogen, which was bubbled through the water head in the graduated burette and is saturated with water (at a temperature of 20-25° C.). The quantity of water fed together with the hydrogen was of 48.8 mg, corresponding to a water:metallic Pd weight ratio of about 33.5:1.

The flask was vigorously stirred at 700 rpm while maintaining a temperature of 30° C. through a cooling water bath.

The catalyst was filtered off and the organic solvent was evaporated to obtain hydrogenated cardoon oil.

After 50 minutes the conversion of linoleic acid was 90.1% and the selectivity towards C18 monounsaturated acid was of 88.3%.

The invention claimed is:

1. Process for the catalytic hydrogenation of a vegetable oil wherein the oil is placed in contact with molecular hydrogen in the presence of a catalyst comprising supported metallic Palladium, wherein said process is performed in the presence of an amount of water in an amount between 5:1 and 100:1 with respect to the weight of metallic Palladium, and at a temperature from 0° C. to 130° C.

2. Process according to claim 1, wherein said process is performed in the presence of an amount of water from 7:1 to 50:1 with respect to the weight of metallic Palladium.

3. Process according to claim 1, wherein the hydrogenation is performed in the presence of 30 mg/kg-500 mg/kg of metallic Palladium with respect to the vegetable oil.

4. Process according to claim 1, wherein said catalyst comprises 0.1-1% by weight of metallic Palladium.

5. Process according to claim 1, wherein said metallic Palladium is supported on a support selected from the group consisting of alumina, carbon, CeO$_2$, ZrO$_2$, CrO$_2$, TiO$_2$, silica, inorganic-organic sol-gel matrix, polycrystalline oxide substrates, amorphous carbon, zeolites, aluminosilicates, alkaline earth carbonates such as magnesium carbonate, calcium carbonate or barium carbonate, barium sulphate, montmorillonites, polymeric matrices, multifunctional resins, ceramic supports.

6. Process according to claim 5, wherein the catalyst comprises metallic Palladium supported on alumina or on carbon.

7. Process according to claim 1, wherein said process is performed at a molecular hydrogen pressure from 1 to 15 bar.

8. Process according to claim 1, wherein said process is performed at a temperature from 70 to 130° C. and at hydrogen pressure from 1 to 6 bar.

9. Process according to claim 1, wherein said process is performed at temperatures from 0 to 50° C., at hydrogen pressures of from 1 to 2 bar, and in the presence of an organic solvent.

10. Process according to claim 9 wherein the organic solvent is selected from hydrocarbons, esters, ketones.

11. Process according to claim 1, wherein said vegetable oil is selected from the group consisting of soya oil, olive oil, castor oil, sunflower oil, peanut oil, maize oil, palm oil, jatropha oil, cardoon oil, cuphea oil, Brassicaceae oil, *Lesquerella* oil, waste frying oils, exhausted vegetable oils or mixtures thereof.

12. A process for the conversion of a polyunsaturated fatty acid into a monounsaturated fatty acid of a vegetable oil, which comprises hydrogenating the vegetable oil with at least a catalyst comprising metallic Palladium, said hydrogenating being performed in presence of an amount of water between 5:1 and 100:1 with respect to the weight of the metallic Palladium.

13. Process according to claim 12 wherein the vegetable oil is selected from the group consisting of sunflower oil, oil from Brassicaceae, cardoon oil or mixtures thereof.

14. An oxidative cleavage process wherein the staring material comprises a vegetable oil obtained from the process according to claim 1.

15. A vegetable oil which comprises:
   a di-unsaturated acid content of less than 10% by weight with respect to the total fatty acids content;
   a mono-unsaturated acid content of more than 70% by weight with respect to the total fatty acids content;
   a trans monounsaturated isomer content higher than 1.5% and lower than 12% by weight with respect to the total fatty acids content.

16. A vegetable oil according to claim 15 wherein the mono-unsaturated acids comprise more than 80% of 9-cis and 12-cis isomers.

17. An oxidative cleavage process wherein the staring material comprises the vegetable oil of claim 15.

18. Process according to claim 2, wherein the hydrogenation is performed in the presence of 30 mg/kg-500 mg/kg of metallic Palladium with respect to the vegetable oil.

19. Process according to claim 2, wherein said catalyst comprises 0.1-1% by weight of metallic Palladium.

* * * * *